(12) United States Patent
Burke (10) Patent No.: US 8,541,186 B2
(45) Date of Patent: Sep. 24, 2013

(54) CANCER DETECTION METHODS AND TECHNIQUES

(75) Inventor: Michael Dan Burke, Sunderland (GB)

(73) Assignee: Care Technologies Inc., Victoria, British Columbia (CA)

( * ) Notice: Subject to any disclaimer, the term of this patent is extended or adjusted under 35 U.S.C. 154(b) by 323 days.

(21) Appl. No.: 12/858,964

(22) Filed: Aug. 18, 2010

(65) Prior Publication Data

US 2011/0045494 A1 Feb. 24, 2011

Related U.S. Application Data

(63) Continuation of application No. PCT/GB2009/000463, filed on Feb. 20, 2009.

(51) Int. Cl.
*G01N 33/574* (2006.01)

(52) U.S. Cl.
USPC .......................................... 435/7.23; 435/7.1

(58) Field of Classification Search
None
See application file for complete search history.

(56) References Cited

U.S. PATENT DOCUMENTS

| | | | | |
|---|---|---|---|---|
| 6,242,203 B1 * | 6/2001 | Melvin et al. | ................ | 435/7.23 |
| 6,284,219 B1 * | 9/2001 | Ajami | ........................... | 424/1.11 |
| 6,346,550 B2 * | 2/2002 | Potter et al. | .................... | 514/685 |
| 7,666,982 B2 * | 2/2010 | Okochi et al. | ................ | 530/324 |
| 7,914,988 B1 * | 3/2011 | Chudin et al. | ............... | 435/6.11 |

FOREIGN PATENT DOCUMENTS

| WO | WO 00/56773 A1 | 9/2000 |
|---|---|---|
| WO | WO 02/30951 A2 | 4/2002 |

OTHER PUBLICATIONS

Doostdar et al, Toxicology, 2000, 144:31-38.*
Potter et al, Br J Cancer, 2002, 86:774-778.*
Kim et al, Arch Pharm Res, 2005, 28:1114-1121.*
Jiang et al, Anal Chim Acta, 2007, 605:70-79.*
C. H. Tung et al., "In vivo Imaging of proteolytic enzyme activity using a novel molecular reporter", Cancer Research, Sep. 1, 2000, vol. 60, No. 17, pp. 4953-4958.
G. I. Murray et al., "Tumor-specific expression of cytochrome P450 CYP1B1", Cancer Research, Jul. 15, 1997, vol. 57, No. 14, pp. 3026-3031.
International Patent Application No. PCT/GB2009/000463 International Search Report mailed Jul. 10, 2009.
International Patent Application No. PCT/GB2009/000463 Preliminary Report on Patentability mailed Aug. 24, 2010.
Bandiera, S. et al., "Proteosomal degradation of human CYP1B1: effect of the Asn453Ser polymorphism and the post-translational regulation of CYP1B1 expression." Molecular Pharmacology 67, 435-443 (2005).
Carnell, D. et al., "Target validation of cytochrome P450 CYPB1 in prostate carcinoma with protein expression in associated hyperplastic and premalignant tissue." International Journal of Radiation Oncology Biology and Physics 58, 500-509 (2004).
Chaurand, P. et al., "Proteomics in diagnostic pathology: profiling and imaging proteins directly in tissue sections." American Journal of Pathology 165, 1057-1068, Oct. 2004.
Deininger, S-O et al., "Characterization of human gastric cancer by MALDI imaging." (2006). Retrieved from the Internet <URL: http://www.bdal.de/data/files/temp/ABRF06_characterization-of-human-gastric-cancer.pdf>.
Gibson, P. et al., "Cytochrome P450 1B1 (CYP1B1) is overexpressed in human colon adenocarcinomas relative to normal colon: implications for drug development." Molecular Cancer Therapeutics 2, 527-534 (2003).
Hoang, M. D. et al., "Cytochrome P450 CYP1B1 expression in human cervical intraepithelial neoplasia. TTV." British Journal of Cancer 85 (Suppl 1), 78 (2001).
Jiang, J. et al., "An immunoaffinity tandem mass spectrometry (iMALDI) assay for detection of *Francisella tularensis*." Analytica Chimica Acta 605, 70-79 (2007).
Koopmann, J. et al., "Serum diagnosis of pancreatic adenocarcinoma using surface-enhanced laser desorption and ionization mass spectrometry." Clinical Cancer Research 10, 860-868 (2004).
Maecker, B. et al., "The shared tumor-associated antigen cytochrome P450 1B1 is recognized by specific cytotoxic T cells." Blood 102, 3287-3294 (2003).
McFadyen, M. et al., "Cytochrome P450 CYP1B1 over-expression in primary and metastatic ovarian cancer." British Journal of Cancer 85, 242-246 (2001).
McFadyen, M. et al., "Immunohistochemical localization of cytochrome P450 CYP1B1 in breast cancer with monoclonal antibodies specific for CYP1B1." Journal of Histochemistry and Cytochemistry 47, 1457-1464 (1999).
National Academy of Clinical Biochemistry Presents Laboratory Medicine Practice Guidelines: Use of Tumor Markers in Clinical Practice: Quality Requirements. (2009). Retrieved from the Internet: <URL: http://www.aacc.org/AACC/members/nacb/LMPG/OnlineGuide/DraftGuidelines/TumorMarkers/TumorMarkersPDF.htm>.
Nedelkov, D. et al., "Population proteomics: the concept, attributes and potential for cancer biomarker research." Molecular and Cellular Proteomics 5, 1811-1818 (2006).

(Continued)

*Primary Examiner* — Mark Halvorson
(74) *Attorney, Agent, or Firm* — Woodard, Emhardt, Moriarty, McNett & Henry LLP (57) ABSTRACT

A method is provided for detecting and/or measuring the occurrence of an enzyme in the form of CYP1B1 in a patient for the detection of cancer in said patient. The method includes the steps of administering a reporter substrate to a patient; taking a bodily fluid and/or tissue sample from the patient after one or more pre-determined periods of time; and analyzing the bodily fluid and/or tissue sample in vitro for the occurrence and/or measurement of a metabolite of the reporter substrate caused as a result of metabolism of the reporter substrate by said enzyme in said patient during said pre-determined period of time.

18 Claims, 7 Drawing Sheets

(56) References Cited

OTHER PUBLICATIONS

Stoeckli, M. et al., "Imaging mass spectrometry; a new technology for the analysis of protein expression in mammalian tissues." Nature Medicine 7, 493-496, Apr. 2001.

Tokizane, T. et al., "CYP1B1 is overexpressed and regulated by hypomethylation in prostate cancer." Clinical Cancer Research 11, 5793-5801 (2005).

Tsuchiya, Y. et al., "MicroRNA regulates the expression of human cytochrome P454 1B1." Cancer Research 66, 9090-9098 (2006).

Warren, E. et al., "An MS-based immunoaffinity approach for quantitation of protein expression and modification levels." Retrieved from the Internet <URL: http://www.med.miami.edu/mnbws/documents/WarrenSR05.pdf>, 2008.

* cited by examiner

SEQUENCE LISTING

<160> NUMBER OF SEQ ID NOS: 10

<210> SEQ ID NO 1
<211> LENGTH: 12
<212> TYPE: PRT
<213> ORGANISM: Homo sapiens

<400> SEQUENCE: 1

Gln Val Leu Glu Gly His Val Leu Ser Glu Ala Arg
1               5                   10

<210> SEQ ID NO 2
<211> LENGTH: 11
<212> TYPE: PRT
<213> ORGANISM: Homo sapiens

<400> SEQUENCE: 2

Glu Leu Leu Ser His Asn Glu Glu Phe Gly Arg
1               5                   10

<210> SEQ ID NO 3
<211> LENGTH: 9
<212> TYPE: PRT
<213> ORGANISM: Homo sapiens

<400> SEQUENCE: 3

Tyr Ser His Asp Asp Pro Glu Phe Arg
1               5

<210> SEQ ID NO 4
<211> LENGTH: 9
<212> TYPE: PRT
<213> ORGANISM: Homo sapiens

<400> SEQUENCE: 4

Asn Phe Ser Asn Phe Ile Leu Asp Lys
1               5

<210> SEQ ID NO 5
<211> LENGTH: 11
<212> TYPE: PRT
<213> ORGANISM: Homo sapiens

<400> SEQUENCE: 5

Ala Ala Gly Asp Ser His Gly Gly Gly Ala Arg
1               5                   10

-continued

```
<210> SEQ ID NO 6
<211> LENGTH: 8
<212> TYPE: PRT
<213> ORGANISM: Homo sapiens

<400> SEQUENCE: 6

Glu Leu Val Ala Leu Leu Val Arg
1               5

<210> SEQ ID NO 7
<211> LENGTH: 7
<212> TYPE: PRT
<213> ORGANISM: Homo sapiens

<400> SEQUENCE: 7

Tyr Pro Asp Val Gln Thr Arg
1               5

<210> SEQ ID NO 8
<211> LENGTH: 8
<212> TYPE: PRT
<213> ORGANISM: Homo sapiens

<400> SEQUENCE: 8

Ala Asn Pro Asn Glu Pro Ala Lys
1               5

<210> SEQ ID NO 9
<211> LENGTH: 6
<212> TYPE: PRT
<213> ORGANISM: Homo sapiens

<400> SEQUENCE: 9

Val Asn Val Thr Leu Arg
1               5

<210> SEQ ID NO 10
<211> LENGTH: 6
<212> TYPE: PRT
<213> ORGANISM: Homo sapiens

<400> SEQUENCE: 10

Val Val Ser Gly Gly Arg
1               5
```

CANCER DETECTION METHODS AND TECHNIQUES

CROSS REFERENCE TO RELATED APPLICATION

This application is a continuation of International Application No. PCT/GB2009/000463, filed Feb. 20, 2009, which claims the benefit of Great Britain Application No. 0803071.0, filed Feb. 20, 2008, the entire disclosures of which are hereby incorporated by reference.

REFERENCE TO SEQUENCE LISTING

This application includes as part of the originally filed subject matter a Sequence Listing filed herewith the application. The Sequence Listing is identical to the Sequence Listing filed in International Application No. PCT/GB2009/000463. The contents of the Sequence Listing are hereby incorporated by reference.

BACKGROUND

This invention relates to improved detection methods and techniques for detecting cancer in a human and/or animal patient.

There are a number of methods that are currently used to allow cancer to be detected and/or diagnosed in a human patient. One such detection method is by a patient or medically trained personnel manually detecting an unusual growth or lump on a part of their body or patient's body respectively using their hand or hands. Once detected, the patient then has to undergo various tests to confirm whether the lump or growth is malignant. A problem with this technique is that a growth or lump is often only detected at a late stage of cancer development when the lump or growth is relatively large. In addition, it only allows for cancer to be detected in certain parts of a patient's body and relies on the patient regularly checking parts of their body in order to realize that a lump or growth is present. Furthermore, due to the location of some cancerous lumps or growths, the patient may feel too embarrassed to get a lump or growth checked by medical personnel at a sufficiently early stage of the cancer development for treatment to be successful.

A further conventional method of cancer detection includes scanning or screening one or more parts of a patient's body. This is an expensive technique and is therefore normally only undertaken on patients with a high risk of developing a particular type of cancer. In addition, scanning or screening can only currently be used to detect certain types of cancer, such as breast cancer, and typically cancers that are at a relatively late stage of development.

The visual examination of tissue biopsies or samples, such as cervical smear tests, is a further method of cancer detection. However, a problem with this method is that the biopsies or smear tests are invasive and often fail to sample the cancerous cells, particularly when the cancer is at an early stage.

A relatively new area of cancer detection is the biochemical measurement of cancer-specific tumour marker proteins in tissue samples, blood or other bodily fluids taken from patients. This detection method has potential advantages over existing detection techniques in that it may be able to detect early stages of cancer. However, since it is still an emerging technology, it is expensive and relatively few types of cancers have so far been detected using this methodology. In addition, an initial cancer diagnosis using tumour marker proteins currently still has to be verified using biopsies or other bodily samples taken from the patient.

Cancer (or tumour) markers are proteins that are produced by cancer cells in significantly greater or lesser quantities than by non-cancer cells. Tumour-specific proteins may be actively secreted by the tumour cells or released into the circulatory system of the patient by necrosis and apoptosis of these cells. Either of these conditions is thought to lead to an alteration of the serum protein profile of the patient (1). As such, it is considered that the detection of cancer markers in blood and other bodily fluids could be a major component of the future of cancer diagnosis despite the abovementioned problems.

Current research and development of cancer markers has so far focused on tumour marker proteins that are specific to a particular type of cancer, with the aim of identifying said cancer type in a patient. A serious limitation of this current approach is that only particular types of cancer can be detected for which the specific markers have been discovered and validated. Since there is likely to be a large number of possible cancer markers for the different types of human cancers, and because the discovery and validation of cancer markers is currently a costly and prolonged enterprise, cancer detection using tumour protein markers is so far of limited use only.

Therefore, it can be seen that despite impressive scientific, medical and technological achievements over the past few decades, cancer is still a leading cause of death, largely because most cancers are diagnosed when disease is advanced. The current problem is that existing methods of cancer detection are unable to detect cancerous growth at a sufficiently early stage of development.

It is therefore an aim of the present invention to provide a method of detecting cancer in a human and/or animal patient using a universal cancer marker.

It is a further aim of the present invention to provide a method of detecting cancer at any stage in the cancer development, and particularly to detecting cancer at a relatively early stage of the cancer development.

It is a yet further aim of the present invention to provide a method of detecting cancer in a human and/or animal patient using blood, urine and/or other bodily fluid or tissue samples taken from said patient.

A further major problem is that the majority of anticancer drugs are excessively toxic to the patient. It is therefore an aim of the present invention to provide a method for determining the quantity or dosage of anticancer drugs and/or treatment which is more specific to a patient's requirements.

BRIEF SUMMARY

According to a first aspect of the present invention there is provided a method for detecting and/or measuring the occurrence of an enzyme in a patient either directly or indirectly by measuring the presence of the enzyme, or at least a part or fragment thereof or any antibody, peptide, other enzyme associated reagent and/or at least one product of the enzyme's metabolic activity, characterized in that the enzyme is CYP1B1.

The detection of the occurrence of the CYP1B1 enzyme, a fragment thereof or any antibody, peptide, other CYP1B1 associated reagent and/or at least one product of the CYP1B1's catalytic or metabolic activity provides an indication of the presence of the CYP1B1 enzyme and thus cancer in the patient. Once detected, an amount of the CYP1B1 enzyme, a fragment thereof or any antibody, peptide, other CYP1B1 associated reagent and/or at least one product of the CYP1B1's catalytic activity can be measured in the sample to determine the degree of cancer in the patient and/or determine a suitable drug dosage or treatment plan.

The basis for the present invention is that the enzyme CYP1B1 appears to be highly over-expressed in all primary human tumours, yet is only minimally expressed, to the extent of being often undetectable, in normal critical tissues (2-3). As such, the present applicants have identified CYP1B1, or at least a part of fragment of CYP1B1, as a potential universal tumour marker protein. In one aspect of the present invention, the applicants have used the CYP1B1 in a method for detecting and/or measuring cancer in a patient.

For example, in different types and grades of breast cancer, CYP1B1 has been found to be present in the tumour cells of 77% of samples from 60 patients, yet was undetectable in stromal cells of connective tissue taken from these patients (4). CYP1B1 was found to be strongly expressed in 100% of 22 bladder cancers (moderate to high grade), yet was absent from the surrounding stromal tissue taken from these patients (5). In various types and grades of ovarian cancer it was present in over 92% of primary tumours from 172 patients, yet remained undetectable in normal ovarian tissue taken from the patients (6).

The applicants consider that the use of CYP1B1 as a tumour (cancer) marker will distinguish cancer cells and tissues from normal cells and tissues to a greater degree than currently used cancer protein markers. The presence of CYP1B1 in a patient can be used as an indication that said patient has some form of cancer present in their body and, because CYP1B1 is over-expressed in both precancerous cells and metastases (6-8), its applicability as an indicator of cancer will span from early to advanced stages of cancer development.

The ability to use CYP1B1 in cancer detection is surprising since it is believed amongst certain research groups in the scientific community that CYP1B1 is highly over expressed not only in cancer cells but also in normal cells. These claims are virtually all based on the measurement of mRNA in humans or of proteins in experimental animals (often pre-dosed with known inducers of CYP1B1), coupled with an apparent assumption that the presence of mRNA in a cell guarantees the presence also of the protein that the mRNA codes for, or that experimental animals are an infallible biochemical model for humans. However, independent research has shown that the above assumption is likely to be incorrect (2). Since then a few further examples have been published of proteins for which the mRNA is found in both normal and diseased cells but the protein coded by the mRNA is present only in one of the normal cells or the diseased cells but not both cell types. At least three evidence-based hypotheses have recently been published to provide possible explanations for this anomaly. These include:

(i) transcriptional regulation by hypo-methylation of the promoter/enhancer region of the CYP1B1 gene (9);
(ii) post-transcriptional regulation by proteosomal degradation of CYP1B1 protein in normal cells, targeted through polyubiqutination of the protein (10); and the most convincing explanation that
(iii) micro-RNA (itself a relatively newly discovered type of RNA) "switches off" the mRNA in normal cells (so that its presence does not lead to the generation of protein) but leaves the mRNA in cancer cells "switched on" (so that it does lead to protein) (11).

Although CYP1B1 is an intracellular enzyme, located on the endoplasmic reticulum, peptide fragments appear on the cancer cell surface (12). Cancer cells will release CYP1B1 peptide fragments into the blood. By the same token, CYP1B1 peptide fragments should be released into the urine by bladder cancer or into semen by prostate cancer. However, the concentration of peptide fragments in blood, urine or semen is likely to be low and only detectable using highly specialized, ultra-sensitive apparatus. As such, a further aspect of the present invention is to provide the means necessary to detect and measure CYP1B1 catalytic products and/or peptide fragments even at very low concentrations in bodily fluid or tissue samples, such as for example in blood, urine and semen, and assess the bodily presence of cancer.

According to a second aspect of the present invention there is provided a method for detecting and/or measuring the occurrence of an enzyme CYP1B1 or at least a part or fragment thereof or any antibody, peptide and/or other CYP1B1 associated reagent or product of the catalytic activity of the enzyme CYP1B1 in a patient either directly or indirectly, wherein the means of detection includes the use of immunotandem mass spectrometry (iMALDI).

iMALDI is a technique of extraordinarily high sensitivity (20). Use of fine needle aspirates drawn from a solid tumour tissue is a routine diagnostic cancer technique.

However, such aspirates present a problem in that the cancer cells they contain are often present in such low levels and are highly contaminated with normal tissue, blood cells, tissue debris and/or the like which serve to confuse and degrade the analysis. Use of the iMALDI technique overcomes the above problem and allows the detection and/or measuring of CYP1B1 peptide fragments in individual cells, such as those sampled using a fine needle tissue aspirate and can therefore be used to determine the presence of cancer in a patient.

More specifically, the mass spectrometry method used in the present invention can be used to detect, diagnose, evaluate, assess, grade, stage and/or measure the presence of cancer in a patient.

More detailed explanation and basis for the mass spectrometry techniques used with the present invention can be found in the following references, the disclosures of which are incorporated by reference herein; The ultra-sensitive detection of proteins, including cancer markers, and their peptide fragments, using mass spectrometry, especially when prefaced by immunoaffinity enrichment (13-15) and "Mass spectrometry has the potential to revolutionize cancer diagnostics by facilitating biomarker discovery, enabling tissue imaging and quantifying biomarker levels" (1).

A further conventional method of diagnosing cancer has been the visual identification of morphologically abnormal cells in tissue biopsies. Specific histological stains for tumour markers are increasingly being used in this context in an attempt to add a molecular dimension to biopsy evaluation. Although histological stains can provide a cell-by-cell visual analysis of a biopsy section, they suffer from a very limited sensitivity and are unlikely to detect markers except when these are present at high levels per cell. The imaging mass spectrometry techniques used in the present invention are able to detect even a few molecules of cancer markers in a single cell of microscope-type sections of tissue biopsies, and can map cancer markers cell-by-cell across the section (16-19).

REFERENCES

1. National Academy of Clinical Biochemistry guidelines: the use of MALDI-TOF mass spectrometry profiling to diagnose cancer.
2. Tumor-specific expression of cytochrome P450 CYP1B1. G I. Murray, M C. Taylor, M C E. McFadyen, et al., Cancer Research 57, 3026-3031 (1997).

3. Cytochrome P450 1B1 (CYP1B1) is overexpressed in human colon adenocarcinomas relative to normal colon: implications for drug development. P. Gibson, J H. Gill, P A. Khan, et al., Molecular Cancer Therapeutics 2, 527-534 (2003).
4. Immunohistochemical localization of cytochrome P450 CYP1B1 in breast cancer with monoclonal antibodies specific for CYP1B1. M. McFadyen, S. Breeman, S. Payne, et al., Journal of Histochemistry and Cytochemistry 47, 1457-1464 (1999).
5. Target validation of cytochrome P450 CYPB1 in prostate carcinoma with protein expression in associated hyperplastic and premalignant tissue. D. Carnell, R. Smith, F. Daley, et al., International Journal of Radiation Oncology Biology and Physics 58, 500-509 (2004).
6. Cytochrome P450 CYP1B1 over-expression in primary and metastatic ovarian cancer. M. McFadyen, M. Cruickshank, I. Miller, et al., British Journal of Cancer 85, 242-246 (2001).
7. Cytochrome P450 CYP1B1 expression in human cervical intraepithelial neoplasia. T T V. Hoang, M D. Burke, M. Ball, et al., British Journal of Cancer 85 (Suppl 1), 78 (2001).
8. Cytochrome P450 CYP1B1 in colon tumorigenesis. LA. Stanley, M. Ball, J. Eaden, et al., Drug Metabolism Reviews 33 (Suppl 1), 77 (2001).
9. CYP1B1 is overexpressed and regulated by hypomethylation in prostate cancer. T. Tokizane, H. Shiina, M. Igwa, et al., Clinical Cancer Research 11, 5793-5801 (2005).
10. Proteosomal degradation of human CYP1B1: effect of the Asn453Ser polymorphism and the post-translational regulation of CYP1B1 expression. S. Bandiera, S. Weidlich, V. Harth, et al., Molecular Pharmacology 67, 435-443 (2005).
11. MicroRNA regulates the expression of human cytochrome P450 1B1. Y. Tsuchiya, M. Nakajima, S. Takagi, et al., Cancer Research 66, 9090-9098 (2006).
12. The shared tumor-associated antigen cytochrome P450 1B1 is recognized by specific cytotoxic T cells. B. Maecker, D H. Sherr, R H. Vonderheide, et al., Blood 102, 3287-3294 (2003).
13. Serum diagnosis of pancreatic adenocarcinoma using surface-enhanced laser desorption and ionization mass spectrometry. J. Koopman, Z. Zhang, N. White, et al., Clinical Cancer Research 10, 860-868 (2004).
14. An MS-based immunoaffinity approach for quantitation of protein expression and modification levels. E. Warren and C. Borchers
15. Population proteomics: the concept, attributes and potential for cancer biomarker research. D. Nedelkov, U A. Kiernan, E E. Niederkofler, et al., Molecular and Cellular Proteomics 5, 1811-1818 (2006).
16. Imaging mass spectrometry; a new technology for the analysis of protein expression in mammalian tissues. M. Stoeckli, P. Chaurand, D E. Halahan, et al., Nature Medicine 7, 493-496.
17. Proteomics in diagnostic pathology: profiling and imaging proteins directly in tissue sections. P. Chaurand, M E. Sanders, R A. Jensen and R M. Caprioli. American Journal of Pathology 165, 1057-1068.
18. The use of mass spectra for cancer biomarker detection. H. Roder, J. Grigorieva and M. Tsypin. (2005).
19. Characterization of human gastric cancer by MALDI imaging. S-O. Deininger, M. Schurenberg, M. Ebert and C. Rocken. (2006).
20. An immunoaffinity tandem mass spectrometry (iMALDI) assay for detection of *Francisella Tularensis*. J. Jiang, C E Parker, J R Fuller et al., Analytica Chimica Acta 605, 70-79 (2007).

DETAILED SUMMARY OF THE PRESENT INVENTION

According to an aspect of the present invention there is provided a method for detecting and/or measuring the occurrence of an enzyme in a patient, the method including the steps of:

a) administering a reporter substrate to the patient;
b) taking a bodily fluid and/or tissue sample from the patient after one or more pre-determined periods of time;
c) analyzing the bodily fluid and/or tissue sample in vitro for the occurrence and/or measurement of a metabolite of the reporter substrate caused as a result of metabolism of the reporter substrate by an enzyme in the patient.

Preferably the enzyme is CYP1B1.

The above technique is typically described as phenotyping. As such, the present invention provides a method of cancer detection and measurement using CYP1B1 as a universal tumour marker using phenotyping.

According to an aspect of the present invention there is provided a method for detecting and/or measuring the occurrence of the enzyme CYP1B1 in a patient sample in vitro, said method including the step of analyzing a patient's bodily fluid and/or tissue sample in vitro for the occurrence and/or measurement of a metabolite of a reporter substrate known to be metabolized by CYP1B1 in the human or animal patient.

The reporter substrate can be specifically administered or taken by the patient prior to testing or the natural occurrence of the reporter substrate in the patient's diet can be relied upon for the purposes of testing.

In one embodiment the reporter substrate is a naturally derived product or substrate. Further preferably the reporter substrate is a plant derived compound. However, the reporter substrate could be bio-synthesized, such as for example from isotopically or non-isotopically labeled feedstocks, products or synthesized chemically as appropriate.

The reporter substrate can be administered orally to the patient and/or via any other suitable route.

Preferably the reporter substrate used includes any or any combination of a stilbene, flavonoid, tannin and/or the like.

In one embodiment the reporter substrate is luteolin and the reporter metabolite is 6-hydroxy-luteolin. The luteolin is typically not metabolized in normal mammalian cells and is excreted from the patient in urine a pre-determined time after being administered. However, in cancerous mammalian cells, the luteolin is metabolized by the CYP1B1 enzyme to produce 6-hydroxy-luteolin which is then excreted from the patient in urine a pre-determined time after being administered.

In one embodiment the reporter substrate is a methoxylated flavone, such as eupatorin. The eupatorin is metabolized by the CYP1B1 enzyme to 0-desmethyleupatorin and formaldehyde. The formaldehyde is subsequently bioconverted to carbon dioxide in the patient's body and is then exhaled in the patient's breath. Thus, in one aspect of the present invention, there is provided a method of cancer detection and measurement using CYP1B1 as a universal tumour marker using carbon dioxide breathtesting.

The pre-determined period is such that the reporter substrate has sufficient time to enter the digestive tract of a patient, be absorbed by the patient's digestive system into the bloodstream, be taken up by one or more of the patient's cells and the reporter substrate or a metabolite of the reporter substrate be excreted into the patient's urine or bodily fluid. For example, this time period can be between 30 minutes and 48 hours.

Detection of a reporter metabolite indicates the presence of the enzyme in the patient from whom the bodily fluid and/or tissue sample has been taken and therefore the presence of cancerous cells in the patient.

In one embodiment the ratio of the amount of the reporter metabolite to the amount of the reporter substrate or other product is measured in the bodily fluid and/or tissue sample. An increase in the ratio can indicate the presence of metabolism of the reporter substrate and thus, the presence of cancerous cells in the patient. For example, in one example, the ratio of a radio isotope or stable isotope labeled reporter substrate or metabolite to a natural or non-isotope labeled reporter substrate or metabolite can be used.

It will be appreciated that the reporter substrate and/or reporter metabolite may be excreted from the patient's body in the form of conjugates.

The bodily fluid and/or tissue samples used can include any or any combination of exhaled patient breath or air, blood, plasma, serum, urine, faeces, semen, saliva, fine needle aspirates, biopsies, tissue sections and/or the like. The body fluid and/or tissue sample can be taken from the patient after a pre-determined time period or a number of samples can be taken at pre-determined time periods.

In one embodiment the in vitro sample taken from the patient is immuno-enriched using the CYP1B1 and one or more antibodies, peptides, reagents and/or the like prior to or during analyzing and/or measuring the same for the presence of a metabolite or reporter substrate of CYP1B1. For example, antibodies (monoclonal and/or polyclonal) against the CYP1B1, reporter substrate and/or metabolites can be used. These antibodies bind with the CYP1B1, reporter substrate and/or metabolites to increase the sensitivity of the detection of the same.

In one embodiment the amount of the CYP1B1, reporter substrate and/or reporter metabolite is measured and/or detected using an iMALDI technique. In a further embodiment the amount of the CYP1B1, reporter substrate and/or reporter metabolite is measured and/or detected using high performance liquid chromatography (hplc).

Further preferably the iMALDI technique is modified by using antibodies which are added prior to or during the analyzing and/or measuring step to isolate and/or concentrate the CYP1B1, reporter substrate and/or the reporter metabolite. These antibodies bind with the CYP1B1, reporter substrate and/or metabolite(s) to increase the sensitivity of the detection of the same.

Thus, in one aspect of the present invention there is provided a method of using iMALDI to measure non-proteinaceous natural compounds, such as for example luteolin, eupatorin, flavonoids, stilbenes, their metabolites and/or the like.

Preferably the antibodies are substantially immobilized on insoluble beads, such as for example by covalent bonding to Sepharose beads during or prior to the analyzing and/or measuring step.

In one embodiment an isotopically labeled reporter substrate is administered to the patient, thereby increasing the sensitivity of detection of the CYP1B1 enzyme. This results in at least one isotopically labeled reporter metabolite being produced in the presence of the CYP1B1 enzyme. For example, $^{13}C$-luteolin or $^{2}H$-luteolin could be used as reporter substrates. The presence of the $^{13}C$ or $^{2}H$ isotopic label increases the sensitivity by improving the signal to noise ratio in the mass spectrometry detection technique.

In one embodiment a tandem gas chromatograph-isotope selective mass spectrometer is used to measure a gaseous reporter metabolite, such as for example isotope labeled carbon dioxide produced by a patient.

The patient can include any mammalian patient, such as a human or animal.

According to a further aspect of the present invention there is provided a method for detecting and/or measuring cancer in a patient, said method including the steps of detecting the presence of a cancer association protein, at least a fragment of said cancer associated protein, antibody, peptide, protein or enzyme associated reagent and/or a metabolite or catalytic product of said cancer associated protein in an in vitro bodily fluid or tissue sample taken from a patient, wherein the cancer associated protein is CYP1B1.

According to a further aspect of the present invention there is provided use of CYP1B1 or a CYP1B1 metabolite or catalytic product thereof for the detection and/or measuring of cancer in a patient.

The method(s) of the present invention can be used to detect and/or measure CYP1B1 activity and/or evaluate, assess, grade, stage the presence of cancer in a patient.

In one embodiment a computer run algorithm is used to facilitate the diagnosis and measurement of cancer.

According to a yet further aspect of the present invention there is provided apparatus for use in said methods.

BRIEF DESCRIPTION OF THE DRAWINGS

A detailed description of embodiments of the present invention will now be described with reference to the accompanying figures, wherein.

DESCRIPTION OF THE SELECTED EMBODIMENTS

Figure 1:
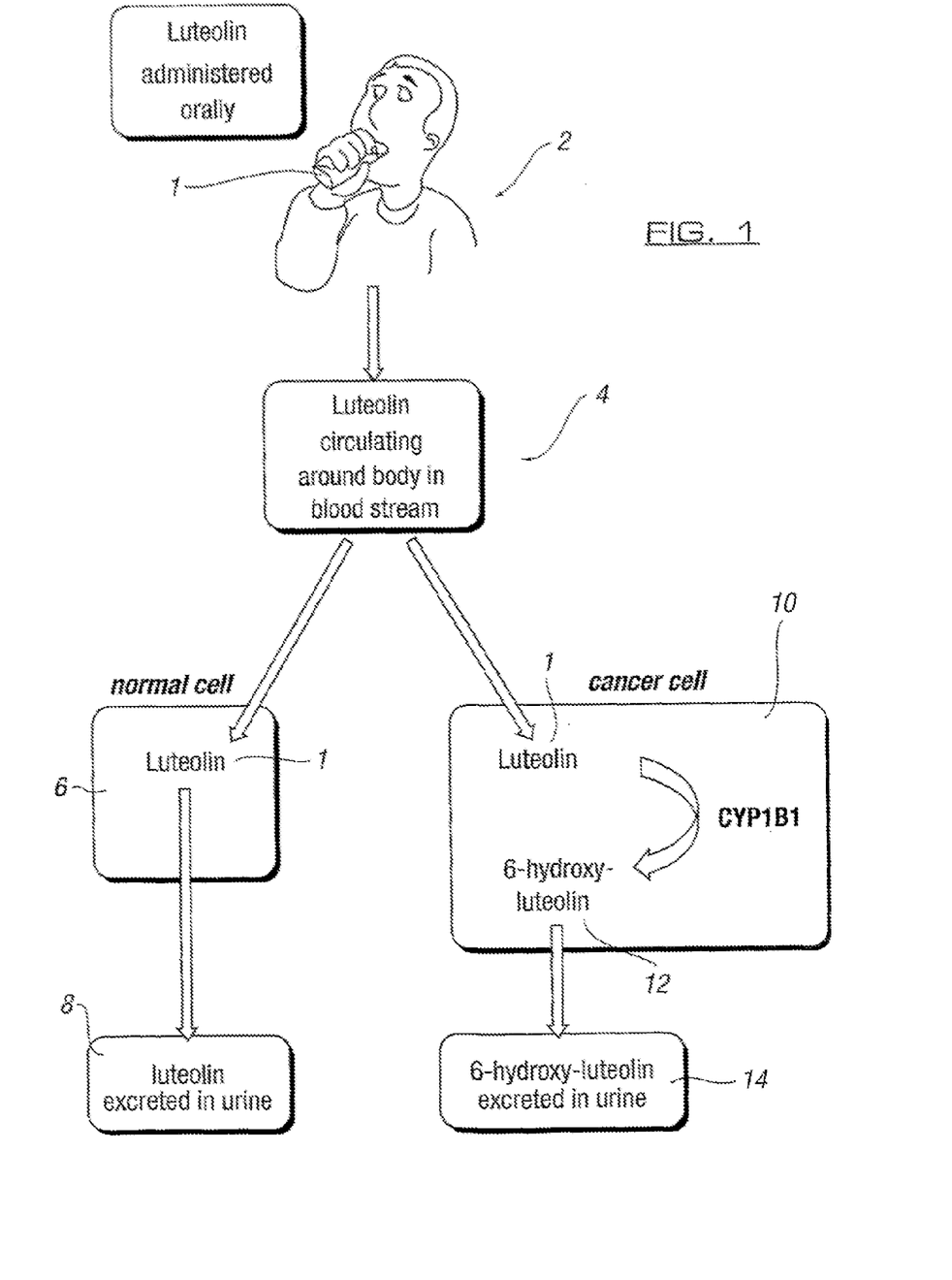
FIG. 1 is a simplified drawing showing the catalytic steps of CYP1B1 with luteolin in a human body according to the present invention.

Referring firstly to FIG. 1, there is illustrated a method for detecting and/or measuring the occurrence of the CYP1B1 enzyme activity in a patient by measuring the catalytic product of the CYP1B1 enzyme on a reporter substrate luteolin which is a natural dietary plant derived compound.

In the method, luteolin 1 is administered orally to a patient 2, the luteolin is digested and passes into the blood stream from the digestive tract for circulation in the blood stream, as shown by the arrow in step 4. Since CYP1B1 is virtually exclusive to cancer cells, when the luteolin passes into a normal cell 6 of the patient 2, the luteolin passes out of the cell and is excreted in the patient's urine 8. A urine sample taken from the patient will show no or negligible catalytic breakdown of the luteolin via a CYP1B1 enzyme if the patient does not have cancer. Since CYP1B1 is present in cancerous cells, when the luteolin passes into a cancerous cell 10, the CYP1B1 enzyme biotransforms (metabolizes) the luteolin to produce 6-hydroxy-luteolin 12 (a reporter metabolite). The 6-hydroxy-luteolin is then excreted in the patient's urine 14. Analysis of a urine sample taken from the cancer patient will show that the luteolin has been metabolized and that the patient has cancer.

More particularly, presence of the reporter substrate and/or metabolite is measured in the urine sample by using antibodies to isolate and concentrate the luteolin and 6-hydroxy-luteolin from the urine prior to processing the samples using an iMALDI technique.

A single urine sample can be taken or a number of urine samples can be taken over a pre-determined time period. When the expected levels of the luteolin and/or 6-hydroxy-luteolin in the urine are sufficiently high, the sample can be analyzed by routine high performance liquid chromatography (hplc). If however the levels of luteolin and/or 6-hydroxy-luteolin in the urine are very low, the samples can be analyzed by iMALDi.

If iMALDI is used, the urine sample is mixed with deuterated luteolin and deuterated 6-hydroxy-luteolin, followed by mixing with bead immobilized antibodies to luteolin and 6-hydroxy-luteolin in order to isolate and concentrate both compounds. The beads are then harvested and, after appropriate washing, are loaded onto the sample plate of a mass spectrometer and dried in place. Finally, luteolin and 6-hydroxy-luteolin are released from the antibody beads into the mass spectrometer flight path and are measured according to their mass. An increase in the urinary ratio between 6-hydroxy-luteolin and luteolin will indicate the presence of cancer cells somewhere in the patient.

Figure 2:
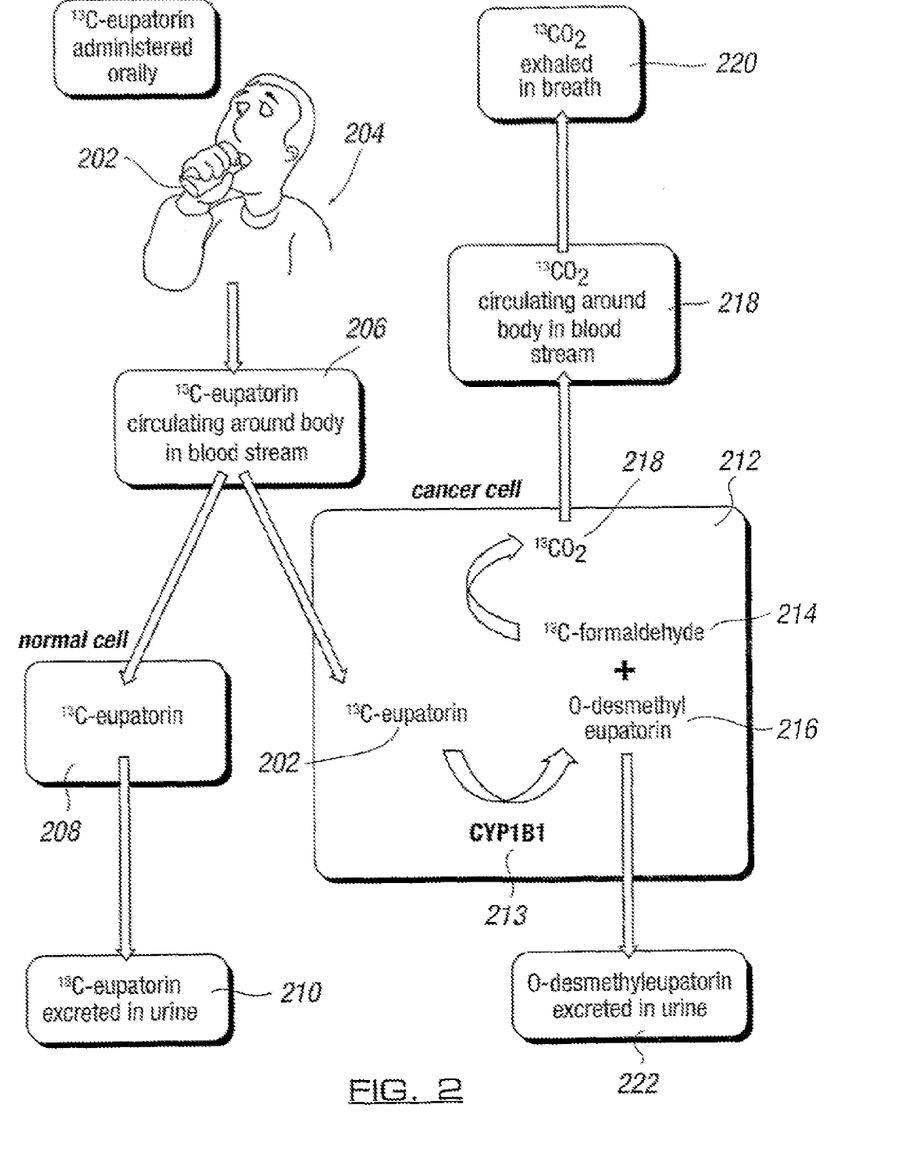
FIG. 2 is a simplified drawing showing the catalytic steps of CYP1B1 with $^{13}C$-eupatorin according to the present invention.

Referring to FIG. 2, there is illustrated a method for detecting and/or measuring the occurrence of the CYP1B1 enzyme activity in a patient by measuring the catalytic product of the CYP1B1 enzyme on an isotopic labeled reporter substrate Eupatorin, which is a methoxylated flavone.

In the method shown in FIG. 2, $^{13}C$-Eupatorin 202 is administered orally to a patient 204, the $^{13}C$-Eupatorin is digested and passes into the blood stream from the digestive tract for circulation in the blood stream of the patient, as shown by the arrow in step 206. Since CYP1B1 is virtually exclusive to cancer cells, when the $^{13}C$-Eupatorin passes into a normal cell 208 of the patient, the $^{13}C$-Eupatorin passes out of the cell and is excreted in the patient's urine 210. A urine sample taken from the patient will show no or negligible catalytic breakdown of the $^{13}C$-Eupatorin via a CYP1B1 enzyme if the patient does not have cancer. Since CYP1B1 is present in cancerous cells, when the $^{13}C$-Eupatorin passes into a cancerous cell 212, the CYP1B1 enzyme 213 metabolizes the $^{13}C$-Eupatorin to produce $^{13}C$-formaldehyde 214 and isotopic labeled O-desmethyleupatorin 216 (reporter metabolites). The $^{13}C$-formaldehyde is converted to isotopic labeled carbon dioxide 218 by the patient's body and exhaled in the patient's breath, as shown by arrow 220. The O-desmethyleupatorin is excreted in the patient's urine 222.

The major isotope of carbon in naturally occurring substances is $^{12}C$. By administering synthetic or biosynthetic eupatorin in which the metabolically leaved methoxy group contains a $^{13}C$ isotopic label in the resultant formaldehyde and carbon dioxide metabolites, the ratio between $^{13}C$ and $^{12}C$ will be significantly higher in the carbon dioxide derived from metabolism of eupatorin than in normal exhaled carbon dioxide. Consequently an increase in the measured ratio of $^{13}C$ and $^{12}C$ of exhaled carbon dioxide following eupatorin administration indicates the presence of CYP1B1 enzyme and therefore the presence of cancer in the patient. Alternatively, the presence of O-desmethyleupatorin can be detected in a urine sample taken from the patient.

The ratio of the exhaled gases is typically measured using, for example, a tandem gas chromatograph-isotope selective mass spectrometer.

Figure 3A:
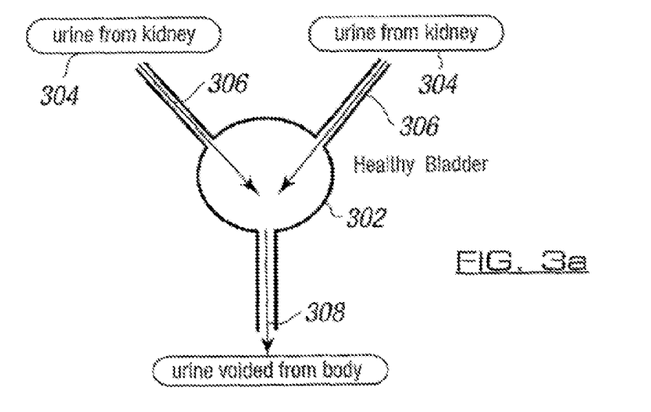
FIGS. 3a-3c show simplified drawings of normal urine production from a human bladder, urine production from patient with bladder cancer and a detailed view of a normal bladder cell and cancerous bladder cell respectively.
Figure 3B:
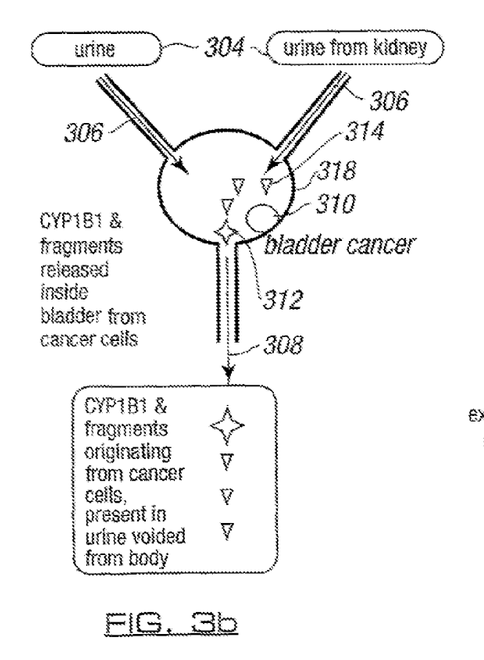
Figure 3C:
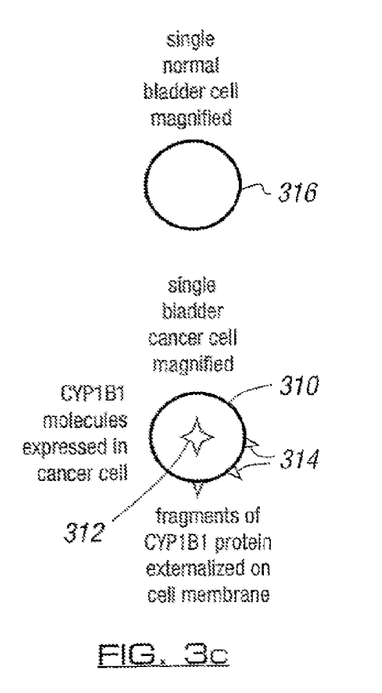

Referring to FIGS. 3a-3c, there is illustrated a method for detecting and/or measuring the occurrence of CYP1B1 enzyme by measuring peptide fragments of CYP1B1 released from cancerous bladder cells into a patient's urine.

More particularly, in FIG. 3a a normal healthy patient's bladder 302 is shown. Urine passes into the bladder from the patient's kidneys 304, as shown by arrows 306, and passes out of the bladder 302 to be excreted from the patient's body, as shown by arrow 308.

In a cancerous bladder cell 310, CYP1B1 protein 312 is expressed in the cell and fragments of the CYP1B1 protein 314 are externalized on the cell surface, as shown in FIG. 3c. This is in contrast to a normal bladder cell 316 which does not have any externalized CYP1B1 protein. As urine 304 passes into a cancerous bladder 318, the CYP1B1 protein 312 and fragments 314 are mixed in the urine and are excreted from the patient in the urine 308. As such, detection of the CYP1B1 protein and/or protein fragments indicates the presence of cancer in the patient.

Due to the low levels of the CYP1B1 protein and/or protein fragments in the urine, a technique such as iMALDI is used. Thus, in one aspect of the present invention there is provided a method of detecting and measuring bladder cancer in a patient using CYP1B1 in urine as a tumour marker by the method of proteomics using iMALDI.

Bioinformatic Selection of CYP1B1 Peptide Sequences Suitable for Multiple Reaction Monitoring SMRM) Analysis MRM analysis is a highly specific mass spectrometry technique useful for quantifying pre-defined peptides of interest. A signal is registered from the spectrometer when a pre-defined fragment ion arised from the pre-defined precursor. The majority of peptides produced by enzymatic digestion (metabolism) are amenable to MRM analysis.

The cytochrome P450 protein superfamily consists of many members and it was therefore necessary to determine the amino acid sequence identity of the CYP1B1 isoform versus other cytochrome P450 isoforms. Analyzing the amino acid sequence of CYP1B1 (Accession number: Q16678, CYP1B1.1 or wild type) using a Basic Local Alignment Search Tool (BLASTp) reveals that CYP1B1 is closer in identity to CYP1B1 isoforms from other species (e.g. 98% identity to chimp and 81% to mouse) than to other cytochrome P450 isoforms in human (e.g. 40% identity). A search against only human sequences reveals that CYP1B1 has the highest identity to its other two family members: 40% identity to CYP1A1 and 39% to CYP1A2. This identity is very low, revealing a lack of long identical peptide sequences that are shared between these isoforms.

A BLASTp analysis was performed and the results show alignment of the CYP1B1 peptide sequence with the most highly scoring human isoforms.

These results show that the amino acid sequence identity of CYP1B1 to other human isoforms contains numerous amino acid sequence differences resulting in mass differences of tryptic peptides that can be exploited by mass spectrometry. However, in selecting peptides for assay development, we took into account polymorphic amino acid variants that have been reported for the different CYP1B1 alleles in the human population. Additionally, the protein does not have reported or predicted extensive post-translational modifications.

UniProt and Ensembl databases show polymorphic variants and known post translational features for the CYP1B1 protein.

MRM analysis was based on the observation of peptides resulting from trypsin cleavage of CYP1B1. To be able to detect the CYP1B1 protein by MRM analysis irrespective of which CYP1B1 allele is present in the sample, tryptic peptides containing polymorphic variations were not selected for assay development and were excluded from the list of usable peptides. Peptides containing amino acid residues susceptible to chemical modifications during sample handling, such as cysteine and methionine, were additionally excluded. Therefore, by excluding polymorphic variants, peptides containing Cys or Met, and selecting for peptide sequences unique within the human proteome, 12 peptides that could be used for the development of an MRM CYP1B1 assay remained. Due to the limits in length during peptide synthesis, peptides 3 through 12 were pursued as optimal candidates.

Synthesis and MRM optimization of natural forms of all 10 CYP1B1 peptides was then completed. Table 1 below shows the 10 CYP1B1 peptides listed in sequential order for Sequence ID Nos. 1-10, respectively.

TABLE 1

| LIMS ID | Peptide sequence | Position | Status |
|---|---|---|---|
| NAT6059A1 | QVLEGHVLSEAR | 164-175 | MRM selection complete |
| NAT6059A2 | ELLSHNEEFGR | 223-233 | MRM selection complete |
| NAT6059A3 | YSHDDPEFR | 214-222 | MRM selection complete |
| NAT6059A4 | NFSNFILDK | 267-275 | MRM selection complete |
| NAT6059A5 | AAGDSHGGGAR | 304-314 | MRM selection complete |
| NAT6059A6 | ELVALLVR | 176-183 | MRM selection complete |
| NAT6059A7 | YPDVQTR | 349-355 | MRM selection complete |
| NAT6059A8 | ANPNEPAK | 495-502 | MRM selection complete |
| NAT6059A9 | VNVTLR | 518-523 | MRM selection complete |
| NAT6059A10 | VVSGGR | 125-130 | MRM selection complete |

A mixture of all the above 10 peptides was made and analyzed by 2 differing mass spectrometry (MS) approaches to determine the relative signal intensity of each peptide (ionization efficiency) in order to focus development efforts on CYP1B1 peptides with the highest sensitivity.

Figure 5:
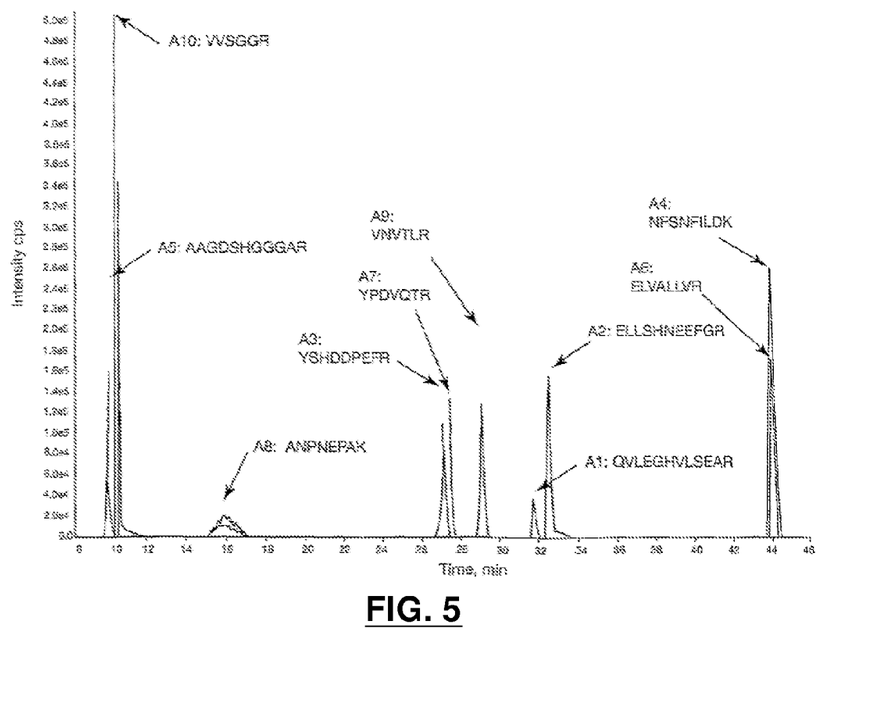
FIG. 5 shows the results of an MRM analysis (Liquid Chromatography MRM/Mass spectrometry LC-MRM/MS) of an approximately equimolar mixture of 10 CYP1B1 peptides (A1-A10) selected for CYB1P1 assay development.

FIG. 5 shows the results of an MRM analysis (Liquid Chromatography MRM/Mass spectrometry LC-MRM/MS) of an approximately equimolar mixture of 10 CYP1B1 peptides (A1-A10) selected for CYB1P1 assay development. Each peak represents the signal observed for recursor fragment (Q1/Q3) ion pair. The five most intense precursor/fragment (Q1/Q3) ion pairs were used for each peptide. MRM signals specific to a peptide should co-elute and stack. This data established the retention time of each peptide and their relative intensities. Currently peptides A4-A6 & A10 appear to be the most intensely observed peptides by MRM. (Note that peptides >6 amino acids in length will be needed for antibody generation.

Figure 6:
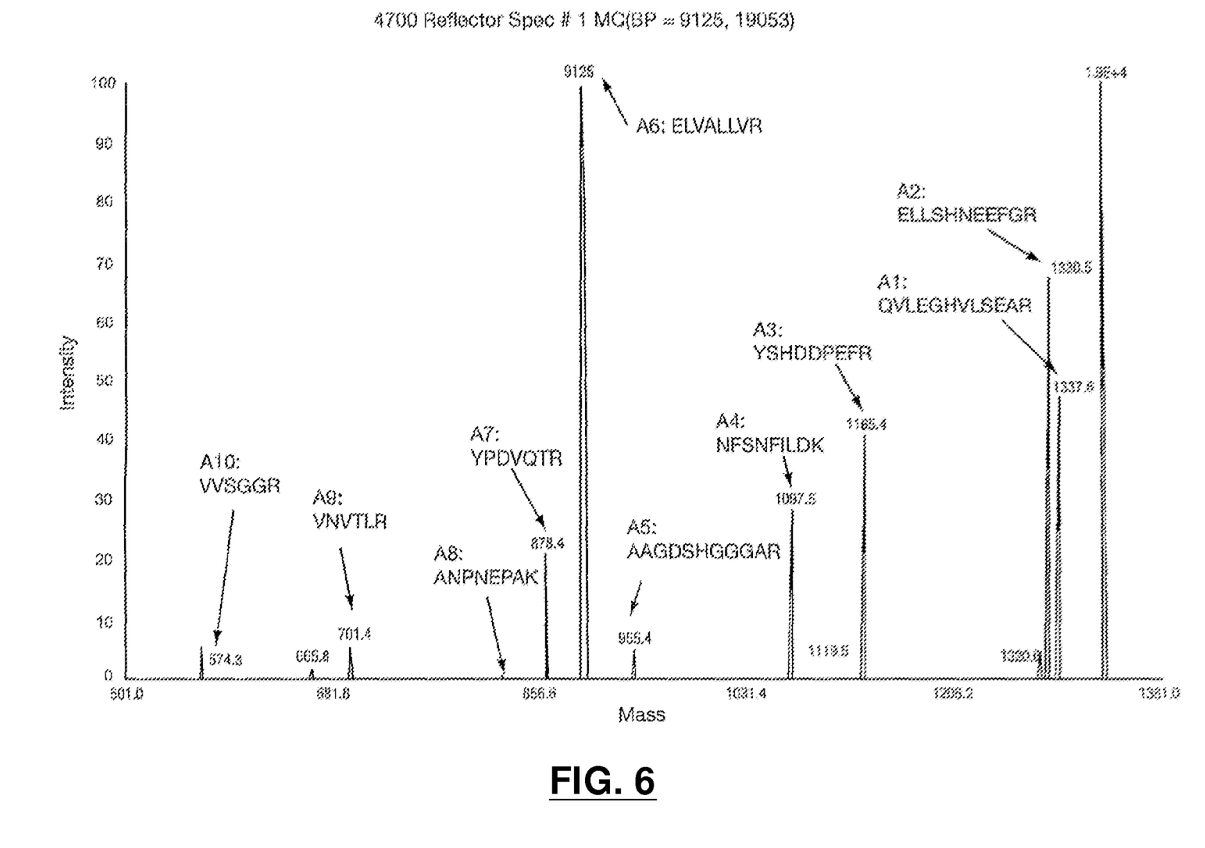
FIG. 6 shows the results of MALDI-TOF analysis of an approximately equimolar mixture of 10 CYP1B1 peptides selected for CYP1B1 assay development, the sequence ID Nos. are shown in a reverse sequential order.

FIG. 6 shows the results of MALDI-TOF analysis of an approximately equimolar mixture of 10 CYP1B1 peptides selected for CYP1B1 assay development. Peptides A1-A4 and A6 appeared to be the most intensely observed peptides by MALDI.

Figure 7:
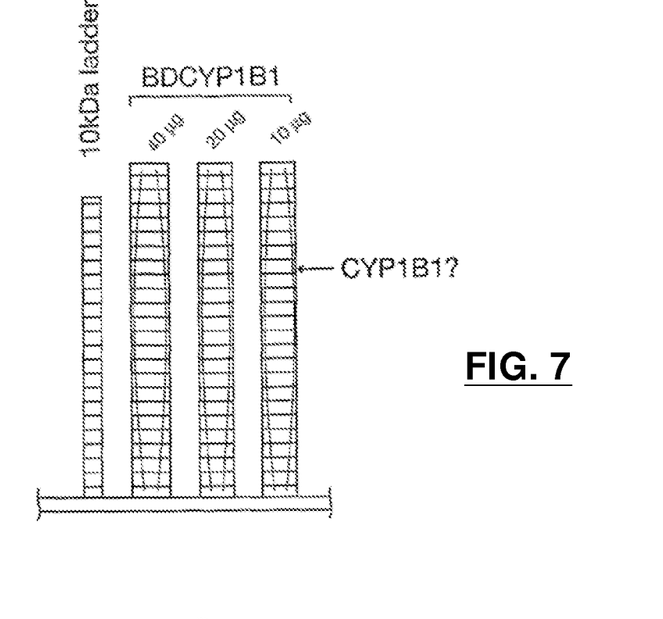
FIG. 7 shows the results of a SDS-PAGE (sodium dodecyl sulphate-polyacrylamine gel electrophoresis) analysis of a microsomal fraction of insect cells containing baculovirus expressed CYP1B1 (Becton Dickson) by reducing SDS-PAGE analysis.

FIG. 7 shows the results of a SDS-PAGE (sodium dodecyl sulphate-polyacrylamine gel electrophoresis) analysis of a microsomal fraction of insect cells containing baculovirus expressed CYP1B1 (Becton Dickson) by reducing SDS-PAGE analysis (4-12% polyacrylamide Invitrogen NuPage Bis-Tris gel). Entire sample lanes were cut into 24 gel slices and processed for in gel trypsin digestion using a Genomic Solutions Progest.

Figure 8:
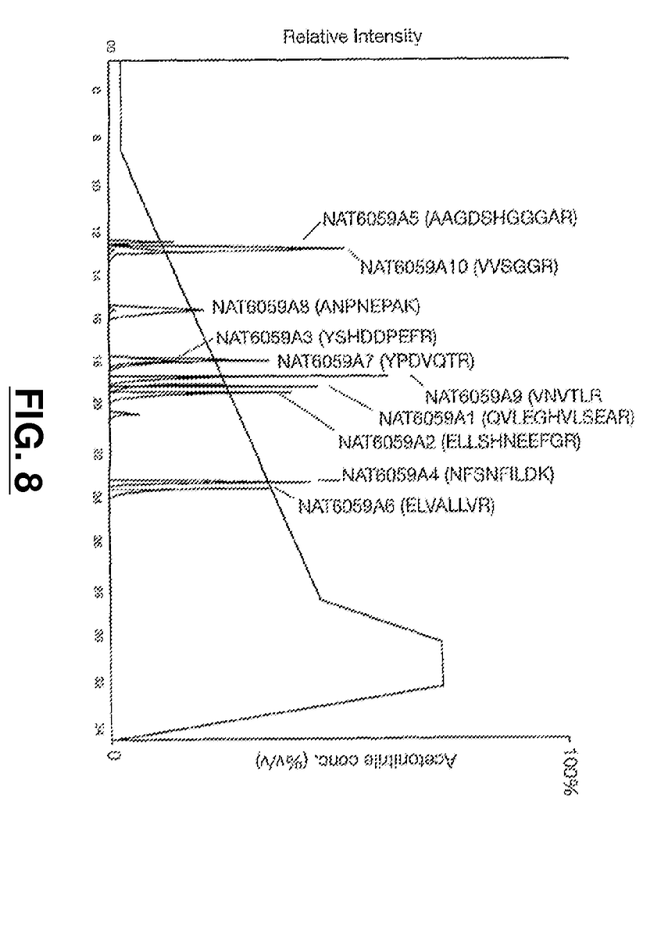
FIG. 8 shows the results of a LC-MRM/MS analysis of gel trypsin digestion of recombinant CYP1B1 (Becton-Dickinson), the Sequence ID Nos. are shown from left to right in the following order: 5, 10, 8, 3, 7, 9, 1, 2, 4, and 6.

FIG. 8 shows the results of a LC-MRM/MS analysis of gel trypsin digestion of recombinant CYP1B1 (Becton-Dickinson). The 5 most intense MRM Q1/Q3 ion pairs were used for all 10 peptides (50 MRM ion pairs total). All 10 peptides were detected well—with NAT6059A3 being the only low signal. The reversed phase gradient is represented as a red line, separation conditions were C18 analytical column (150×0.075 mm), 300 nL/min flow rate.

TABLE 2

| MALDI Intensity Rank | MRM Intensity Rank | Peptide Name | mw | Most Intense Q1/Q3 Ion Pair | Peak Width (sec) | Retention Time | Combined Rank |
|---|---|---|---|---|---|---|---|
| 1 | 7 | NAT6059A6 (ELVALLVR) | 911.6 | 456.8/ 571.4 | 7.4 | 23.67 | 8 |
| 2 | 5 | NAT6059A2 (ELLSHNEE FGR) | 1329.6 | 444.2/ 488.2 | 6.1 | 19.57 | 7 |
| 3 | 8 | NAT6059A1 (QVLEGHVL SEAR) | 1336.7 | 446.6/ 555.8 | 6. | 19.28 | 11 |
| 4 | 10 | NAT6059A3 (YSHDDPEFR) | 1164.5 | 389.2/ 322.2 | 5.6 | 17.97 | 14 |
| 5 | 3 | NAT6059A4 (NFSNFILDK) | 1096.6 | 549.3/ 836.5 | 6.2 | 23.49 | 8 |
| 6 | 6 | NAT6059A7 (YPDVQTR) | 877.4 | 439.7/ 358.2 | 8.0 | 18.16 | 12 |
| 7 | 1 | NAT6059A9 (VNVTLR) | 700.4 | 351.2/ 488.3 | 5.7 | 18.88 | 8 |
| 8 | 4 | NAT6059A5 (AAGDSHGG GAR) | 954.4 | 319.1/ 407.2 | 4.5 | 12.64 | 12 |
| 9 | 2 | NAT6059A10 (VVSGGR) | 573.3 | 287.7/ 376.2 | 11.6 | 13.02 | 11 |
| 10 | 9 | NAT6059A8 (ANPNEPAK) | 839.4 | 420.7/ 655.3 | 15.2 | 15.75 | 19 |

Table 2 above shows a summary of CYP1B1 peptide relative intensities by MALDI and MRM (electrospray). MRM intensity rank was determined from an actual trypsin digest of recombinant BD CYP1B1. Retention times during reversed phase separation and half-height peak widths are also listed. Combined rank is the sum of both the MALDI and MRM intensity ranks. Thus, according to one aspect of the present invention there is provided use of one or more of the peptide sequences for CYP1B1 or CYP1B1 metabolites listed above for use in the identification of CYP1B1 in a patient.

In Solution Digestion

"In solution digestion" was used because the protein sample contains no detergent. If the protein sample is in a buffer that contains chemicals incompatible with trypsin activity, a buffer exchange must first be performed using a protein precipitation.

The following solutions were made using the compounds listed in Table 3 below.

TABLE 3

| Item | Manufacturer | Product No. |
|---|---|---|
| Ammonium bicarbonate | Sigma | A6141 |
| Iodoacetamide | Fluka | 57670 |
| Dithiothreitol | Fluka | 43815 |
| Urea | Invitrogen | ZU10001 |
| Thiourea | Invitrogen | ZT10002 |
| Sodium deoxycholate | Sigma | D6750 |
| Trypsin (modified, sequencing grade) | Promega | V5111 |

Solutions

Solubilization Buffers 1. 8 M urea: 8 M urea in 10 mM HEPES, pH 8.0. To make 10 mL, 4.80 g urea and 23.8 mg HEPES were dissolved in 10 mL water. The pH was adjusted with NaOH and the solution was stored at room temperature (i.e. approx. 20-25° C.).
2. 6 M urea/2 M thiourea: 6M urea, 2 M thiourea in 10 mM HEPES, pH 8.0. To make 10 mL, 3.60 g urea, 23.8 mg HEPES and 1.52 g thiourea were dissolved in water. The pH was adjusted as necessary with NaOH. Solutions of thiourea often contain insoluble particles so samples can be centrifuged at 5000×g for 10 minutes to clarify them. The solution was stored at 4° C.
3. 10% w/v sodium deoxycholate in 50 mM ammonium bicarbonate.

Other Buffers

4. Digestion buffer: 50 mM ammonium bicarbonate ($NH_4HCO_3$). To make 10 mL, 40 mg $NH_4HCO_3$ was dissolved in 10 mL water and stored at room temperature.
5. Iodoacetamide stock solution: 0.5 μg/μL iodoacetamide in digestion buffer. To make 10 mL, 5 mg iodoacetamide was dissolved in 10 mL digestion buffer. This was separated into 100 μL, aliquots and stored at −20° C.
6. DTT stock solution: 0.5 μg/μL DTT in water. To make 10 mL, 5 mg DTT in 10 mL was dissolved in water and stored at −20° C.

Steps

1. Solubilize the protein pellet (either precipitated from solution or a centrifuge pellet from a subcellular fractionation) in 8 M urea, 6 M urea/2 M thiourea or 10% sodium deoxycholate. Selection of the particular denaturant will be sample specific but urea/thiourea appeared to work the best for membrane proteins. The volume is kept as small as possible as the final concentration of these chaotropic chemicals will need to be reduced by dilution prior to trypsin addition. (0.5-1.0 μL of solubilization buffer per μg of protein was typically used.). This produces the sample protein.
2. Add 1 μg DTT/50 μg to the sample protein and incubate for 30 mins at room temperature. To avoid sample loss the protein mass in the sample may need to be roughly estimated.
3. Add 5 μg iodoacetamide/50 μg to the sample protein and incubate for 30 mins at room temperature.
4. Samples were then disluted with enough digestion buffer to reduce the urea concentration to 1 M and sodium deoxycholate concentration to 1% w/v.
5. Add 1 μg trypsin/50 μg to the sample protein and incubate overnight (16 h) at 37° C.
6. It was found that digested peptides are best stored at −80° C. while awaiting analysis.

Figure 4:
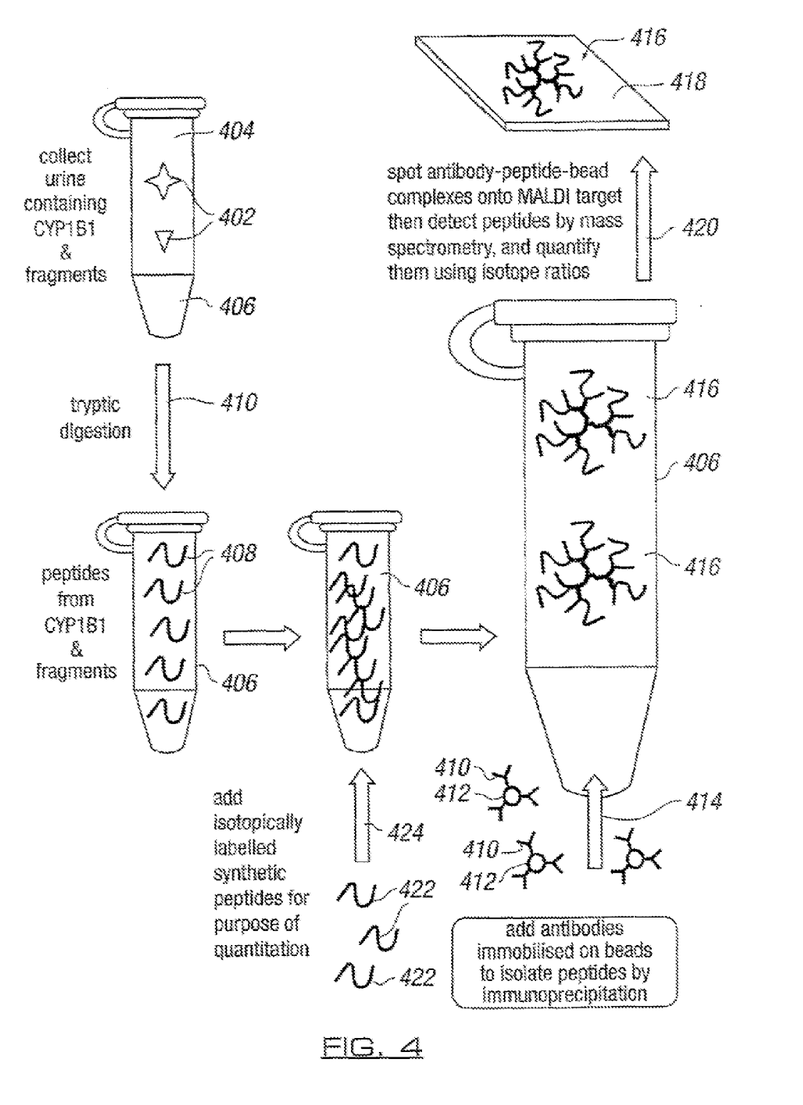
FIG. 4 is a simplified drawing showing the steps involved in detecting and measuring CYP1B1 fragments using a mass spectrometry technique according to the present invention.

Referring to FIG. 4, an example of detection of CYP1B1 protein fragments in an in vitro sample taken from a patient is now described using iMALDI technique.

In this technique, the CYP1B1 protein and/or protein fragments 402 contained in a urine sample in a suitable reservoir or vial 406 are first cleaved into smaller peptides 408 (i.e., light peptides) via tryptic digestion using trypsin as shown by arrow 410. The resulting tryptic peptides 408 are isolated via a suitable technique and concentrated by liganding to specific antibodies 410 that are linked to insoluble beads 412, as shown by arrow 414 and the resulting bonded tryptic peptides/antibody/bead complexes 416. The tryptic peptides/antibody/bead complexes 412 carrying the CYP1B1 tryptic peptides 408 are then harvested and, after appropriate washing, are loaded and dried onto a target plate 418 of a mass spectrometer, as shown by arrow 420. The peptides 408 are then stripped from the antibody beads 410/412 and measured according to their mass. The CYP1B1 fragments are quantified by the ratio between the amounts of heavy and light peptides respectively. It is the initial immuno-isolation and concentration of the tryptic fragments mat gives iMALDI the high level of sensitivity sufficient to measure small amounts of CYP1B1 protein fragments arising from a single cell.

Since mass spectrometry measures peptides by their mass, a synthetic peptide that is isotopically labeled with $^{13}C$ or $^2H$ is distinguishable from an identical naturally occurring peptide, since the latter will be lighter and will contain predominantly $^{12}C$ and $^1H$ isotopes of carbon and hydrogen respectively. Thus, as part of the method shown in FIG. 4, an isotopically labeled substantially identical synthetic peptide 422 can be mixed with the urine derived tryptic peptides 408, as shown by arrow 424 prior to step 414. As such, CYP1B1 is quantifiable using iMALDI by measuring the quantity ratio between the relatively heavier synthetic labeled peptides and the relatively lighter body derived peptides. The greater the amount of CYP1B1 peptides present in the urine sample, the further advanced the cancer is likely to be in the patient.

The antibodies against CYP1B1 or CYP1B1 peptides are covalently immobilized on beads (i.e. Sepharose). The synthetic peptides used in the above process are typically deuterium-labeled synthetic peptides (i.e. heavy peptides) corresponding to the naturally occurring CYP1B1 peptides and are synthesized using $^2H$-labeled FMOC amino acids.

It will be appreciated that the above described technique could be used for other types of cancer, such as prostate cancer which released CYP1B1 protein and fragments into semen. Other cancers release CYP1B1 protein and fragments into a patient's blood from the cancerous cells. Thus, the detection of CYP1B1 in semen indicates the probable presence of prostate cancer, while detection of CYP1B1 in blood indicates some sort of cancer, although further investigation may be required to determine the type and/or location of the cancer.

Thus, in one aspect of the present invention there is provided a method of detecting and measuring prostate cancer in a patient using CYP1B1 in semen as a tumour marker by the method of proteomics using iMALDI. In a further aspect of the present invention there is provided a method of detecting and measuring cancer in a patient using CYP1B1 in blood as a tumour marker by the method of proteomics using iMALDI.

In related procedures of the present invention, the presence of CYP1B1 protein or fragments in the cells of tissue biopsies taken from a patient can be detected either in fine needle biopsies using iMALDI or in microscope-type sections using imaging mass spectrometry. Fine needle aspirates drawn from a solid tumour tissue are subject to tryptic digestion, antibody isolation and mass spectrometry similar to the techniques described above, thereby enabling the detection of the protein in even single cells. Sometimes it may be necessary to analyze the spatial distribution of cancer cells in a tissue biopsy. In these instances, tissue biopsy samples are prepared as for optical microscopic examination but they are then analyzed using imaging mass spectrometry. This detects even a few molecules of CYP1B1 in single cells in the section, thereby providing a 2-D map and quantification of CYP1B1 containing cancer cells or pre-cancer cells across the section.

The tissue biopsy sections are prepared similarly as for optical microscopic examination but with no or minimal fixation (in the latter case the section is cut from frozen tissue) and mounted onto an optically transparent glass target plate of an iMALDI mass spectrometer. If required the section can be stained to allow visual inspection of the tissue morphology. Energy-absorbing matrix for mass spectrometry (i.e. sinapinic acid) is sprayed onto the section and the mass spectrum acquired for many different locations across the section. The mass signal for CYP1B1 is then reconstructed into an image of CYP1B1 density across the section.

Thus, in one aspect of the present invention there is provided a method of detecting and measuring cancer in a patient using CYP1B1 in tissue biopsy sections as a tumour marker by the method of proteomics using imaging mass spectrometry.

The invention claimed is:

1. A method for detecting and/or measuring an occurrence of an enzyme CYP1B1 in a patient, said method comprising the steps of:
   a) administering a reporter substrate to a patient;
   b) taking a bodily fluid and/or tissue sample from the patient after one or more pre-determined periods of time; and
   c) analyzing the bodily fluid and/or tissue sample in vitro for the occurrence and/or measurement of a metabolite of the reporter substrate known to be metabolized by CYP1B1 in the human or animal patient, wherein the reporter substrate includes any or any combination of a luteolin, $^{13}$C-luteolin, $^{2}$H-luteolin, eupatorin or $^{13}$C-eupatorin, and the reporter metabolite is 6-hydroxy-luteolin, desmethyleupatorin, formaldehyde and/or carbon dioxide.

2. A method for detecting and/or measuring an occurrence of an enzyme CYP1B1 in a patient sample in vitro, said method comprising the step of:
   analyzing a patient's bodily fluid and/or tissue sample in vitro for the occurrence and/or measurement of a metabolite of a reporter substrate known to be metabolized by CYP1B1 in the human or animal patient, wherein the reporter substrate includes any or any combination of a luteolin, $^{13}$C-luteolin, $^{2}$H-luteolin, eupatorin or $^{13}$C-eupatorin, and the reporter metabolite is 6-hydroxy-luteolin, and desmethyleupatorin.

3. A method according to claim 1 wherein the reporter substrate is a naturally derived product.

4. A method according to claim 3 wherein the reporter substrate is a plant derived product.

5. A method according to claim 1 wherein the reporter substrate is bio-synthesized.

6. A method according to claim 1 wherein the reporter substrate is an isotopically labeled feedstock or product.

7. A method according to claim 1 wherein the pre-determined period of time is between 30 minutes and 48 hours.

8. A method according to claim 1 further comprising: measuring a ratio of the reporter substrate to the metabolite of the reporter substrate in the bodily fluid and/or tissue sample in vitro.

9. A method according to claim 1 further comprising: measuring a ratio of a radio isotope or stable isotope labeled reporter substrate or metabolite to a natural or non-isotope labeled reporter substrate or metabolite in the bodily fluid and/or tissue sample in vitro.

10. A method according to claim 1 wherein the bodily fluid and/or tissue sample is any one of or any combination of exhaled patient air, blood, plasma, serum, urine, faeces, semen, saliva, fine needle aspirate, biopsies, or tissue section.

11. A method according to claim 1 further comprising: measuring an amount of enzyme CYP1B1.

12. A method according to claim 1 further comprising: measuring and/or detecting the amount of enzyme CYP1B1, reporter substrate and/or reporter metabolite using immunotandem mass spectrometry (iMALDI).

13. A method according to claim 12 wherein antibodies are added to the bodily fluid and/or tissue sample in vitro prior to or during the analyzing and/or measuring step to isolate and/or concentrate the CYP1B1, reporter substrate and/or reporter metabolite.

14. A method according to claim 13 wherein the antibodies are substantially immobilized on insoluble beads prior to and/or during the analyzing and/or measuring step.

15. A method according to claim 1 further comprising:
measuring and/or detecting the amount of enzyme CYP1B1, reporter substrate and/or reporter metabolite using high performance liquid chromatography (hplc).

16. A method according to claim 1 further comprising:
measuring the amount of carbon dioxide using a tandem gas chromatograph-isotope selective mass spectrometer.

17. A method according to claim 1 further comprising:
measuring and/or detecting the amount of enzyme CYP1B1, reporter substrate and/or reporter metabolite using imaging mass spectrometry.

18. A method according to claim 1 for detecting and/or measuring cancer in a patient.

* * * * *

UNITED STATES PATENT AND TRADEMARK OFFICE
CERTIFICATE OF CORRECTION

PATENT NO. : 8,541,186 B2  
APPLICATION NO. : 12/858964  
DATED : September 24, 2013  
INVENTOR(S) : Michael Dan Burke

Page 1 of 1

It is certified that error appears in the above-identified patent and that said Letters Patent is hereby corrected as shown below:

Title Page, add item
"(30)       Foreign Application Priority Data
Feb 20, 2008    (GB) ..........................0803071.0"

In the Claims:
Col. 19, lines 14-15, replace
"11. A method according to claim 1 further comprising: measuring an amount of enzyme CYP1B1."
with --11. A method according to claim 1 further comprising: measuring an amount of enzyme CYP1B1, reporter substrate, and/or reporter metabolite.--

Signed and Sealed this
Twenty-sixth Day of November, 2013

Margaret A. Focarino
*Commissioner for Patents of the United States Patent and Trademark Office*